(12) United States Patent
Fenical et al.

(10) Patent No.: US 7,521,414 B2
(45) Date of Patent: Apr. 21, 2009

(54) POLYOL MACROLIDE ANTITUMOR-ANTIBIOTICS FROM THE MARINE ACTINOMYCETE STRAIN CNQ140

(75) Inventors: William H. Fenical, Del Mar, CA (US); Paul R. Jensen, San Diego, CA (US); Hak Cheol Kwon, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 291 days.

(21) Appl. No.: 10/873,657

(22) Filed: Jun. 21, 2004

(65) Prior Publication Data

US 2004/0266701 A1 Dec. 30, 2004

Related U.S. Application Data

(60) Provisional application No. 60/480,287, filed on Jun. 20, 2003, provisional application No. 60/480,288, filed on Jun. 20, 2003.

(51) Int. Cl.
*A61K 31/00* (2006.01)
*C12P 19/62* (2006.01)

(52) U.S. Cl. .......................... 514/1; 435/76
(58) Field of Classification Search .................. 514/31, 514/99, 175; 435/76
See application file for complete search history.

(56) References Cited

OTHER PUBLICATIONS

Feling et al., Angew. (2003) Angew. Chem. Int. Ed. 42(3):355-357.
Fusetani (ed.): *Drugs from the Sea*. Basel, Karger 2000, pp. 6-29.
Goodfellow and Haynes. "Actinomycetes in Marine Sediments" Ortiz-Ortiz et al., ed. *Biological, Biochemical, and Biomedical Aspects of Actinomycetes*. Academic Press: Orlando 1984, pp. 453-472.
Davidson, B.S., Current Opinion in Biotechnology 1995, 6:284-291.
Blunt, J.W., et al., Nat. Prod. Rep., 2003, 20:1-48.
Bull, A.T., et al., Microbiol. Mol. Bio. Rev., Sep. 2000, pp. 573-606.
Colquhoun, J.A., et al., Extremophiles, 1998, 2:269-277.
Fenical, W., Chem. Rev. 1993, 93:1673-1683.
Fenical, W., Marine Biotechnology 1997, 15:339-341.
Fernandez-Chimeno R.I., et al., Journal of Antibiotics, 2000 53(5):474-478.
Goodfellow and O'Donnell, (1989) Search and discovery of industrially significant actinomycetes. In *Microbial Products: New Approaches, Society for General Microbiology Symposium* No. 44 eds Baumberg, S., et al., pp. 343-383. Cambridge: Cambridge University Press.
Goodfellow and Williams, Ann. Rev. Microbiol. 1983, 37:189-216.
Helmke and Weyland, Int. J. Syst. Bacteriol., 1984, 34(2):127-138.
Horan, A.C. "Aerobic Actinomycetes: A Continuing Source of Novel Natural Products." In Gullo, V.P. (ed.), *The Discovery of Natural Products with Therapeutic Potential*. Boston: Butterworth-Heinemann, 1994, pp. 1-30.
Romero, F., et al., The Journal of Antibiotics, 1997, 50(9):734-737.
Watve, M.G. et al., 2001, Arch. Microbiol 176:386-390.
Weyland, J., Nature, 1969, 223:858..
Zheng, Z, et al., FEMS Microbiology Letters, 2000, 188:87-91.
Jensen, P.R. et al., Appl. Environ. Microbiol., 1991, 57(4):1102-1108.
Mincer, T.J., et al., Appl. Environ. Microbiol., 2002, 68(10):5005-5011.
He, H., et al., J. Am. Chem. Soc., 2001, 123:5362-5363.
Stach, J.E.M., et al., Appl. Environ. Microbiol., 2003, 69(10):6189-6200.
Colquhoun, J.A., et al., Antonie van Leeuwenhoek, 1998, 74:27-40.
Stach, J.E.M. et al., Envion. Microbiol., 2003, 5(10):828-841.
Elliott, P.J. et al., J. Mol. Med., 2003, 81:235-245/.
Joseph, S.J., et al., 2003, Appl Environ. Microbiol. 69(12):7210-7215.
Otoguro, M., et al., J. Appl. Microbiol., 2001, 92:118-130.
Cheng, X.C., et al., J. Nat. Prod., 1999, 62:608-610
Cheng, X.C., et al., J. Nat. Prod. 1999, 62:605-607.
Erba, E., et al., British Journal of Cancer, 1999, 88(7):971-980.
Bernan, V.S., et al., Advances in Applied Microbiology 1997, 43:57-90.
Jenson and Fenical, Annu. Rev. Microbiol 1994, 48:559-84.
Okami, Y., Journal of Marine Biotechnology 1993, 1:59-65.
Goodfellow and O'Donnell, (1988) "Actinomycetes in Biotechnology", Okami, et al., ed., *Search and Discovery of New Antibiotics*. Academic Press: San Diego 1988, pp. 33-67.
Moran, M.A., et al., 1995, Appl environ. Microbiol. 61(10):3695-3700.

*Primary Examiner*—Sandra Saucier
*Assistant Examiner*—Susan Hanley
(74) *Attorney, Agent, or Firm*—DLA Piper LLP (US)

(57) ABSTRACT

A novel family of cyclic polyene natural products isolated from marine actinomycete strain CNQ140 is provided. This novel strain of actinomycetes was obtained from a previously unstudied population of marine actinomycetes that reside in sediments off La Jolla, Calif. Compounds derived from strain CNQ140 have been characterized as having a cyclic polyene-polyol structure; a molecular weight from about 996 to about 1010 in the core ring structure; and at least 58 carbons and at least 14 oxygens. The invention compounds have antitumor and/or anti-microbial activity.

13 Claims, 1 Drawing Sheet

FIG. 1

POLYOL MACROLIDE ANTITUMOR-ANTIBIOTICS FROM THE MARINE ACTINOMYCETE STRAIN CNQ140

RELATED APPLICATIONS

This application claims the benefit under 35 U.S.C. § 119(e) of U.S. provisional patent application 60/480,288, filed Jun. 20, 2003 and 60/480,287, filed Jun. 20, 2003, each of which is incorporated herein by reference in its entirety.

This research was supported in part by the National Institutes of Health, National Cancer Institute, under grant No. CA 44848. The U.S. Government may have an interest in this invention.

BACKGROUND OF THE INVENTION

1. Field of the Invention

This invention relates generally to bacteria as a source of therapeutic compounds and, more particularly, to a new marine actinomycete taxon and to therapeutic compounds derived therefrom.

2. Background

Pharmaceutical researchers have long tapped actinomycetes, gram-positive, soil bacteria with fungal-like filaments, as a source of novel antibiotics and antitumor compounds. In addition, pharmaceutical researchers have long been using natural antibiotics from actinomycetes as models and starting materials for the production of new medicines. Prominent examples are the antibiotics actinomycin, streptomycin, and vancomycin. The repertoire of these microorganisms, previously known to live mainly in soil, has by now been well studied. Approximately 120 drugs have their origins in terrestrial actinomycetes, and although highly prolific for more than 50 years, the chemical diversity from this source began to decline more than 10 years ago.

Marine actinomycetes have only recently been discovered. Like their terrestrial relatives, these organisms make some highly biologically active substances. A U.S. team has recently discovered a new antitumor agent in one of these marine bacteria. The compound salinosporamide A, is a potent inhibitor of several types of human cancers. This compound is produced by marine actinomycete strain CNB-392, a member of this new bacterial genus called "*Salinospora*." *Salinospora* strains have been recovered from muddy sediments collected at depths in excess of 1,000 meters from the Atlantic and Pacific Oceans, the Red Sea, and the Gulf of California. At this depth, there is no light, very high pressure, and low temperature.

New methods have also been developed for sifting through the samples (which contain roughly one billion microorganisms per cubic centimeter), identifying specific microorganisms by genetic methods and screening their metabolic products for anticancer and antibiotic properties. From 100 strains of *Salinospora* preliminarily tested, 80% produced molecules that inhibit cancer cell growth and roughly 35% revealed the ability to kill pathogenic bacteria and fungi. Salinosporamide A, is a powerful inhibitor of certain colon and lung and breast cancers, and it has been shown to act by the inhibition of the intracellular proteasome.

However, culture of marine organisms has proven difficult in the laboratory. A number of explanations have been proposed to explain this phenomenon. From an eco-physiological point of view, it has been argued that there exist obligate oligotrophs that cannot grow in any nutrient rich media, such as is commonly used to grow land bacteria. It has even been proposed that sudden exposure to nutrient rich external conditions induces suicide responses originating from an imbalance between anabolism and catabolism. Thus there is a need in the art for improved methods for isolating and culturing marine bacteria, such as actinomycetes.

Antibiotic resistance of pathogenic bacteria, including pathogenic actinobacteria, such as *Mycobacterium tuberculosis*, is a well-known problem faced by medical practitioners in treatment of bacterial diseases. Therefore, there is a further need in the art for new antibiotics and drugs effective to circumvent resistance to existing antibiotics in treatment of bacterial infections in humans and in other mammals, including domestic and farm animals.

Many types of cancer cells also exhibit drug resistance. Accordingly, there is also an urgent need for new anticancer agents, for example, those with new pharmacological properties and unusual structures that may be found.

SUMMARY OF THE INVENTION

The present invention is based on the discovery that certain fermentation products of the marine actinomycete strain CNQ140 are effective inhibitors of hyperproliferative mammalian cells and pathogenic bacteria, or both. The CNQ140 strain lies within the new actinomycetes taxon MAR2, which is fully described and characterized in co-pending U.S. Provisional Application Ser. No. 60/514,127, filed Oct. 24, 2003, the content of which is hereby incorporated by reference in its entirety.

Accordingly, in one embodiment, the invention provides therapeutic marine actinomycete-derived compounds characterized as having a unique cyclic polyene-polyol structure; a molecular weight from about 996 to about 1010 in a core region of the cyclic structure; at least 58 carbons and at least 14 oxygens; and anti-cancer and/or anti-microbial activity.

In another embodiment, the invention provides methods for use of an isolated marine actinomycete CNQ140 as deposited at the ATCC under accession number PTA-5276 for drug discovery by culturing the actinomycete CNQ140 and extracting a compound with antitumor and/or antibacterial activity from the conditioned medium in which the actinomycetes CNQ140 is grown.

In another embodiment, the invention provides a medium for culturing marine actinomycetes by admixing:

5 grams starch 4 mL hydrosolubles (50%)

2 grams menhaden meal 2 grams kelp powder 2 grams chitosan 1 liter filtered seawater In yet another embodiment, the invention provides methods for culturing marine actinomycete CNQ140. The actinomycete CNQ140 is cultured in the invention culturing medium for 2 for 7 days with shaking so as to obtain an in vitro culture of the actinomycetes sp. CNQ140.

In another embodiment, there are provided pharmaceutical compositions including at least one compound produced by CNQ140 and having a structure as described herein in a pharmaceutically acceptable carrier.

In another embodiment, there are provided articles of manufacture including packaging material and a pharmaceutical composition contained within the packaging material. The packaging material includes a label indicating that the pharmaceutical composition can be used for treatment of cell proliferative disorders and the pharmaceutical composition includes at least one compound produced by CNQ140 and having a structure as described herein.

DETAILED DESCRIPTION OF THE INVENTION

The present invention answers these needs by providing a new isolated marine actinomycete species CNQ140 useful for isolating therapeutic agents having antibiotic/anticancer activity. This new species of marine actinomycete bacteria was obtained from a previously unstudied population of marine actinomycetes that reside in sediments off La Jolla, Calif. Microbes from very deep marine sediments beyond the continental shelf, having been out of evolutionary contact with terrestrial biota for 3 billion years, possess host toxins for which there are no resistance mechanisms developed in terrestrial bacterial genomes. Thus the invention compounds have novel mechanisms, high efficacy and minimal resistance, overcoming problems with certain current antitumor and antibiotic agents.

In one embodiment, the invention provides a new isolated marine actinomycete species CNQ140 as deposited at the ATCC under accession number PTA-5276 on Jun. 20, 2003.

In another embodiment, there are provided pharmaceutical compositions including at least one compound produced by CNQ140 and having a structure as described herein in a pharmaceutically acceptable carrier therefor.

In another embodiment, there are provided articles of manufacture including packaging material and a pharmaceutical composition contained within the packaging material, wherein the packaging material includes a label which indicates that the pharmaceutical composition can be used for treatment of cell proliferative disorders and wherein the pharmaceutical composition includes at least one compound produced by CNQ140 and having a structure as described herein.

In yet another embodiment, there are provided methods for treating a mammalian cell proliferative disorder. Such a method can be performed for example, by administering to a subject in need thereof a therapeutically effective amount of a compound produced by CNQ140 and having a structure as described herein.

In an additional embodiment, there are provided methods for producing a compound produced by CNQ140 and having a structure as described herein and having the ability to inhibit the proliferation of hyperproliferative mammalian cells. Such a method can be performed, for example, by cultivating a culture of a MAR2 sp. strain CNQ140 (ATCC # PTA-5276), and isolating from the culture at least one compound produced by CNQ140 and having a structure as described herein.

In another embodiment, the invention provides methods for culture and extraction of marine actinomycete strain CNQ140. To culture the invention marine actinomycetes, a special culture broth was developed comprising:

5 grams starch
4 mL hydrosolubles (50%)
2 grams menhaden meal
2 grams kelp powder
2 grams chitosan
1 liter filtered seawater.

The cultivation was for 7 days, with shaking at 215 rpm and at a temperature of 80° F.

Figure 1:
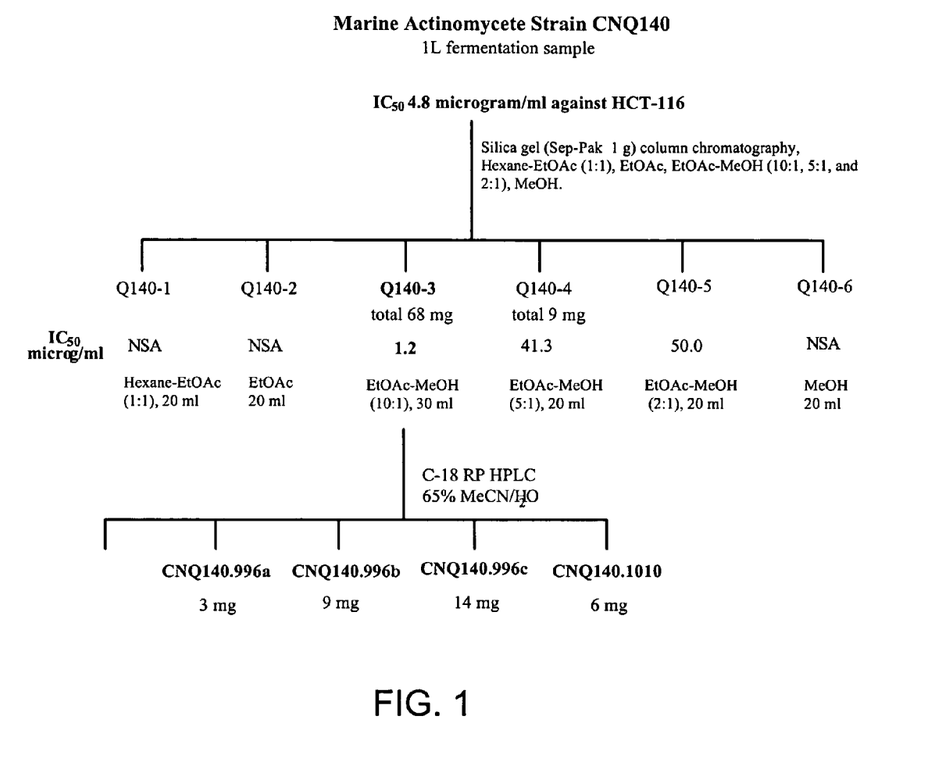
FIG. 1 is a schematic representation of an extraction scheme for obtaining the compounds of the invention from conditioned medium.

For extraction of compounds from the CNQ140 actinomycete, the following protocol was used. Pre-washed XAD-7 resin (20 g) was added to 1 liter of culture and mixed for 1 hour. The contents were collected by filtration, washed with deionized water (1 liter) and eluted with acetone (250 ml). The extraction liquid from each successive extraction step (as shown in FIG. 1) was tested for anticancer activity ($IC_{50}$) against HCT-116 colon cancer cell line. Extraction was performed using the chromatographs and elution solvents shown in FIG. 1. The first step of the extraction yielded an extraction liquid Q140-3, which showed a $IC_{50}$ when tested at a concentration of 1.2 microgram/ml against colon cancer cell line HCT-116. A second extraction step using C-18 reverse phase HPLC and a solvent of 65% MeCN in water yielded four distinct compounds with activity against the colon cancer cell line. These CNQ140-derived compounds kill or substantially inhibit growth of drug resistant pathogenic bacteria as well (See Table 1 below). The chemical structures of these compounds appear below:

CNQ140.996a

-continued

CNQ140.996b

CNQ140.996c

CNQ140.1010

In yet another embodiment the invention provides therapeutic compounds characterized as having a cyclic polyene-polyol structure, a molecular weight from about 996 to about 1010 amu for the core structure, at least 58 carbons and at least 14 oxygens; and anticancer and/or antimicrobial activity. Preferably the compounds have the activity of a macrolide so as to inhibit nucleic acid synthesis in pathogenic bacteria, for example at the 50S ribosome.

As shown by the data in Table 1 below the invention therapeutic compounds have both anticancer and antibiotic activity, as illustrated in tests against HCT-116 human colon adenocarcinoma cancer cells (HCT-116); methicillin resistant *Staphylococcus aureus* (MRSA); and vancomycin-resistant *Enterococcus faecium* (VREF):

TABLE 1

| Compound | HCT-116 ($IC_{50}$ microgm/ml) | MRSA (MIC microgm/ml) | VREF (MIC microgm/ml) |
|---|---|---|---|
| CNQ140.996a | 0.18 | 0.13 | 0.13 |
| CNQ140.996b | 2.9 | 0.25 | 0.63 |
| CNQ140.996c | 2.6 | 0.25 | 0.25 |
| CNQ140.1010 | 3.1 | 0.25 | 0.25 |

Planar chemical structures for four compounds isolated from CNQ140 were determined using such known techniques as heteronuclear multiple bond coherence (HMBC) NMR and HR MALDI-FT mass spectrum as described in Example 2 below, offering a new target for synthetic chemists to focus on. The abundance of alcohol moieties in the invention compounds offers ready sites for formation of derivative compounds by adding such substituents as acyl, substituted acyl, lower alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, or substituted arylalkynyl.

As used herein, the term "acyl" refers to a monovalent straight or branched chain hydrocarbon group having from one to about 12 carbon atoms derived from a carboxylic acid by removal of an OH group.

As used herein, "substituted acyl" refers to acyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like, and "substituted alkyl" refers to alkyl groups further bearing one or more substituents as set forth above.

As used herein, "lower alkyl" refers to alkyl groups having from 1 to about 6 carbon atoms.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "thioalkyl" refers to the moiety —S-alkyl-, wherein alkyl is as defined above, and "substituted thioalkyl" refers to thioalkyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

Exemplary substituted alkyls contemplated for use include halogenated alkyls, such as for example chlorinated alkyls.

As used herein, the terms "purified" and "isolated" each refer to the state of being free, to some extent, of other dissimilar compositions or compounds with which the referenced organisms, compositions, and/or compounds will normally be associated in their natural state, so that upon being "purified" or "isolated" the referenced organisms, compositions, and/or compounds will comprise at least about 0.25%, about 0.5%, about 1%, about 2%, about 4%, about 5%, about 10%, about 20%, about 50%, and at least about 75% of the mass, by weight, of a given sample.

The compounds of the invention may be formulated into pharmaceutical compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference.

The compounds according to this invention may contain one or more asymmetric carbon atoms and thus occur as racemates and racemic mixtures, single enantiomers, diastereomeric mixtures and individual diastereomers. The term "stereoisomer" refers to chemical compounds that differ from each other only in the way that the different groups in the molecules are oriented in space. Stereoisomers have the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. All such isomeric forms of these compounds are expressly included in the present invention.

Indeed, the invention compounds can be derivatized by substituents as described above to improve pharmacokinetic and pharmacodynamic properties, which facilitate administration and increase utility of the derivatives as anti-neoplastic agents. Procedures for chemically modifying invention compounds to produce additional compounds within the scope of the present invention are available to those of ordinary skill in the art.

The invention compounds are fermentation products of the marine actinomycete sp. MAR2, strain CNQ140. MAR2 is a member of the order Actinomycetales, which are high G+C gram positive bacteria. The novelty of CNQ140 is at the genus level. Invention compounds set forth herein are produced by any strain of the MAR2 sp. and preferably by the MAR2 sp. strain CNQ140. To that end, the CNQ140 strain of MAR2 sp. was deposited on Jun. 20, 2003 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. PTA-5276.

As is the case with other organisms, the characteristics of MAR2 sp. are subject to variation. For example, recombinants, variants, or mutants of the specified strain may be obtained by treatment with various known physical and chemical mutagens, such as ultraviolet light, X-rays, gamma rays, and N-methyl-N'-nitro-N-nitrosoguanidine. All natural and induced variants, mutants, and recombinants of the specified strain that retain the characteristic of producing a compound of the invention are intended to be within the scope of the claimed invention.

Invention compounds can be prepared, for example, by bacterial fermentation, which generates the compounds in sufficient amounts for pharmaceutical drug development and for clinical trials. In certain embodiments, therefore, invention compounds can be produced by fermentation of the actinomycete strain CNQ140 in CKA-liquid medium as described in Example 1 below. Essential trace elements that are necessary for the growth and development of the culture should also be included in the culture medium. Such trace elements commonly occur as impurities in other constituents of the medium in amounts sufficient to meet the growth requirements of the organisms. It may be desirable to add small amounts (i.e. 0.2 mL/L) of an antifoam agent such as polypropylene glycol (MW. about 2000) to large scale cultivation media if foaming becomes a problem. The organic metabolites can be isolated by adsorption onto an Amberlite® XAD-16 resin (GFS Chemicals, Powell, Ohio), and many other lipophilic adsorptive resins.

The present invention also provides articles of manufacture including packaging material and a pharmaceutical composition contained within the packaging material, wherein the packaging material comprises a label which indicates that the pharmaceutical composition can be used for treatment of disorders and wherein the pharmaceutical composition includes a compound according to the present invention.

Thus, in one aspect, the invention provides a pharmaceutical composition including a compound of the invention, wherein the compound is present in a concentration effective to treat cell proliferative disorders. The concentration can be determined by one of skill in the art according to standard treatment regimen or as determined by an in vivo animal assay, for example.

Pharmaceutical compositions employed as a component of invention articles of manufacture can be used in the form of a solid, a solution, an emulsion, a dispersion, a micelle, a liposome, and the like, wherein the resulting composition contains one or more invention compounds as an active ingredient, in admixture with an organic or inorganic carrier or excipient suitable for enteral or parenteral applications. Compounds employed for use as a component of invention articles of manufacture may be combined, for example, with the usual non-toxic, pharmaceutically acceptable carriers for tablets, pellets, capsules, suppositories, solutions, emulsions, suspensions, and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semi-solid, or liquid form. In addition auxiliary, stabilizing, thickening and coloring agents and perfumes may be used.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Invention pharmaceutical compositions may be formulated for administration by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. Invention compounds may, for example, be administered in a form suitable for immediate release or extended release. Immediate release or extended release may be achieved by the use of suitable pharmaceutical compositions comprising invention compounds, or, particularly in the case of extended release, by the use of devices such as subcutaneous implants or osmotic pumps. Invention compounds may also be administered liposomally.

The invention further provides methods for using invention antitumor-antibacterial compounds to inhibit the proliferation of mammalian cells by contacting these cells with an invention compound in an amount sufficient to inhibit the proliferation of the mammalian cell. One embodiment is a method to inhibit the proliferation of hyperproliferative mammalian cells. For purposes of this invention, "hyperproliferative mammalian cells" are mammalian cells that are not subject to the characteristic limitations of growth, e.g., programmed cell death (apoptosis). A further preferred embodiment is when the mammalian cell is human. The invention further provides contacting the mammalian cell with at least one invention antitumor-antibacterial compound and at least one additional antineoplastic agent.

In another embodiment, there are provided methods for treating a mammalian cell proliferative disorder, comprising administering to a subject in need thereof a therapeutically effective amount of an invention compound. Cell proliferative disorders that can be effectively treated by the methods of the invention include disorders characterized by the formation of neoplasms. As such, invention compounds are antineoplastic agents. As used herein, "neoplastic" pertains to a neoplasm, which is an abnormal growth, such growth occurring because of a proliferation of cells not subject to the usual limitations of growth. As used herein, "antineoplastic agent" is any compound, composition, admixture, co-mixture or blend that inhibits, eliminates, retards or reverses the neoplastic phenotype of a cell. In certain embodiments, the neoplasms are selected from mammary, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes thyroid and non-Hodgkin's disease, stomach, myeloma, bladder, renal, neuroendocrine which includes thyroid and non-Hodgkin's disease and Hodgkin's disease neoplasms. In one embodiment, the neoplasms are melanoma.

Chemotherapy, surgery, radiation therapy, therapy with biologic response modifiers, and immunotherapy are currently used in the treatment of cancer. Each mode of therapy has specific indications that are known to those of ordinary skill in the art, and one or all may be employed in an attempt to achieve total destruction of neoplastic cells. Chemotherapy utilizing one or more invention MAR2 polyene-polyol compounds is provided by the present invention. Moreover, combination chemotherapy, chemotherapy utilizing invention CNQ140-produced compounds in combination with other neoplastic agents, is also provided by the invention as combination therapy is generally more effective than the use of single antineoplastic agents. Thus, a further aspect of the present invention provides compositions containing a therapeutically effective amount of at least one invention CNQ140-produced compound in combination with at least one other antineoplastic agent. Such compositions can also be provided together with physiologically tolerable liquid, gel or solid carriers, diluents, adjuvants and excipients. Such carriers, diluents, adjuvants and excipients may be found in the United States Pharmacopeia Vol. XXII and National Formulary Vol XVII, U.S. Pharmacopeia Convention, Inc., Rockville, Md. (1989), the contents of which are herein incorporated by reference. Additional modes of treatment are provided in AHFS Drug Information, 1993 ed. by the American Hospital Formulary Service, pp. 522-660, the contents of which are herein incorporated by reference.

Antineoplastic agents that can be utilized in combination with an invention antitumor-antibacterial compound include those provided in The Merck Index, 11 th ed. Merck & Co., Inc. (1989) pp. Ther 16-17, the contents of which are hereby incorporated by reference. In a further embodiment of the invention, antineoplastic agents may be antimetabolites, which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents, which may include, but are not limited to, cyclophosphamide, melphalan, busulfan, paraplatin, chlorambucil, and nitrogen mustard. In a further embodiment of the invention, the anti-neoplastic agents are plant alkaloids, which may include, but are not limited to, vincristine, vinblastine, taxol, and etoposide. In a further embodiment of the invention, the antineoplastic agents contemplated are antibiotics that may include, but are not limited to, doxorubicin (adriamycin), daunorubicin, mitomycin c, and bleomycin. In a further embodiment of the invention, the antineoplastic agents contemplated are hormones, which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the invention, the antineoplastic agents contemplated include enzymes, which may include, but are not limited to, L-asparaginase or aminoacridine derivatives, which may include, but are not limited to, amsacrine. Additional antineoplastic agents include those provided in Skeel, Roland T., "Antineoplastic Drugs and Biologic Response Modifier: Classification, Use and Toxicity of Clinically Useful Agents," Handbook of Cancer Chemotherapy (3rd ed.), Little Brown & Co. (1991), the contents of which are herein incorporated by reference.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated.

The term "therapeutically effective amount" means the amount of the subject compound that will elicit the biological or medical response of a tissue, system, animal or human that is being sought by the researcher, veterinarian, medical doctor or other clinician, e.g., lessening of the effects/symptoms of cell proliferative disorders.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment. Administration of the invention compounds can be prior to, simultaneously with, or after administration of another therapeutic agent or other anti-neoplastic agent.

The invention pharmaceutical compositions used for the administration of the compounds of this invention may conveniently be presented in dosage unit form and may be prepared by any of the methods well known in the art of pharmacy. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets can contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Tablets can also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents, which have been mentioned above. The sterile injectable preparation may also be a sterile injectable solution or suspension in a non-toxic parenterally-acceptable diluent or solvent, for example as a solution in 1,4-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be formulated as suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

For topical use, creams, ointments, jellies, solutions or suspensions, etc., containing the compounds of the present invention are employed.

Compounds and compositions of the invention can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 μg/kg, more usually 0.01 to 10 μg/kg, of the host body weight. Alternatively, dosages within these ranges can be administered by constant infusion over an extended period of time, usually exceeding 24 hours, until the desired therapeutic benefits have been obtained. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The structures of the invention molecules are novel and possess a new type of carbon skeleton providing activity as a macrolide. Various procedures are known in the art for synthesis of macrolides. For example, the following references are devoted to chemical synthesis of this class of molecules: (a) Norcross, R. D.; Paterson, I. Total synthesis of bioactive marine macrolides. *Chem. Rev.* 1995, 95, 2041. (b) Paterson, I.; Florence, G.; Gerlach, K.; Scott, J. P. Total synthesis of the antimicrotubule agent (+)-discodermolide using boron-mediated aldol reactions of chiral ketones. *Angew. Chem. Int. Ed.* 2000, 39, 377. (c) Paterson, I.; Wallace, D. J.; Oballa, R. M. Studies in marine macrolide synthesis: synthesis of a fully functionalized C1-C28 subunit of spongistatin 1 (altohyrtin A). *Tetrahedron Lett.* 1998, 39, 8545. (d) Paterson, I.; Woodrow, M. D.; Cowden, C. J. Studies in marine macrolide synthesis: construction of a 24-membered macrocyclic intermediate for aplyronine A. *Tetrahedron Lett.* 1998, 39, 6041. (e) Paterson, I.; Watson, C.; Yeung, K.-S.; Wallace, P. A.; Ward, R. A. Total synthesis of scytophycin C. *J. Org. Chem.* 1997, 62, 452. (f) Paterson, I.; Yeung, K.-S.; Ward, R. A.; Cumming, J. G.; Smith, J. D. Total synthesis of swinholide A and hemiswinholide A. *J. Am. Chem. Soc.* 1994, 116, 9391. In view of the large body of art concerned with synthesis of such molecules, it is believed that the invention polyol macrolide antibiotic and anticancer agents from the marine actinomycete CNQ140 can be synthesized in the laboratory. In addition, in view of the polyol structure of the invention molecules, those of skill in the art can readily make and test derivatives, for example, addition derivatives of the invention compounds.

In yet another embodiment the invention provides therapeutic compounds characterized as having a cyclic polyene-polyol structure, a molecular weight from about 996 to about 1010 for the core structure, at least 58 carbons and at least 14 oxygens, and anticancer and/or antimicrobial activity. Preferably the compounds have the activity of a macrolide so as to inhibit nucleic acid synthesis in pathogenic bacteria, for example at the 50S ribosome.

As shown by the data in Table 1 below the invention therapeutic compounds have both anticancer and antibiotic activity, as illustrated in tests against HCT-116 colon cancer cells (HCT-116); methicillin resistant *Staphylococcus aureus* (MRSA); and vancomycin-resistant *Enterococcus faecium* (VREF). Non-limiting examples of bioactivity of the invention therapeutic compounds against these organisms are shown in Table 1 below.

TABLE 1

| Compound | HCT-116 ($IC_{50}$ microgm/ml) | MRSA (MIC microgm/ml) | VREF (MIC microgm/ml) |
|---|---|---|---|
| CNQ140.996a | 0.18 | 0.13 | 0.13 |
| CNQ140.996b | 2.9 | 0.25 | 0.63 |
| CNQ140.996c | 2.6 | 0.25 | 0.25 |
| CNQ140.1010 | 3.1 | 0.25 | 0.25 |

The invention is further described in the following non-limiting examples:

EXAMPLE 1

Isolation and Characterization of MAR2 Species, Culture # CNQ140

CNQ140, like other MAR2 clade members, possesses signature nucleotides within its 16S rDNA that separate it phylogenetically from all other genera within the family *Streptomycetaceae*. 16S rRNA signature nucleotides distinguishing the MAR2 clade from all other genera within the *Streptomycetaceae* are as follows:

| Position 16S rRNA (*E. coli* numbering system) | MAR2 clade members | Other *Streptomycetaceae* |
|---|---|---|
| 304 | U | C |
| 626 | U | C |
| 671 | C | U |
| 735 | G | A |
| 1028 | U | C |
| 1033 | A | G |

These signature nucleotides have been determined to be a definitive marker for members of this group, which also have a physiological growth requirement of sodium. Signature nucleotides have been aligned to *E. coli* positions 27-1492 using all existing members of the *Streptomycetaceae* in the Ribosomal Database Project as of Jan. 31, 2001. For the MAR2 clade, 10 sequenced morphotypes all display the signature nucleotides.

Fermentation

CNQ140 was cultured in shaken CKA-liquid medium, 1 liter at 35° C. for 9 days. The formula for CKA medium is as follows:
  5 grams starch
  4 mL hydrosolubles (50%)
  2 grams menhaden meal
  2 grams kelp powder
  2 grams chitosan
  1 liter filtered seawater After 4 days 20 grams Amberlite® XAD-16 resin (Sigma, nonionic polymeric adsorbent) was added.

Extraction

Pre-washed XAD-7 resin (20 g) was added to 1 liter of culture and mixed for 1 hour. The contents were collected by filtration, washed with deionized water (1 liter) and eluted with acetone (250 ml). The extraction liquid from each successive extraction step (as shown in FIG. 1) was tested for anti-cancer activity ($IC_{50}$) against HCT-116 colon cancer cell line. Extraction was performed using the chromatography methods and elution solvents shown in FIG. 1. The first step of the purification yielded fraction Q140-3, which showed a $IC_{50}$ of 1.2 microgm/mL against the HCT-116 colon cancer cell line. A second chromatographic purification step for fraction CNQ140-3, using C-18 reverse phase HPLC and 65% MeCN in water, yielded four distinct CNQ140 macrolide polyol-polyene compounds with activity against the colon cancer cell line:

These CNQ140-produced compounds kill or substantially inhibit growth of drug resistant pathogenic bacteria as well (See Table 1). The chemical structures of these compounds are shown above.

EXAMPLE 2

Purification of an Active Compound

Fraction CNQ140-3 was purified using C-18 reverse phase HPLC and 65% MeCN in water, to yield four distinct CNQ140 macrolide polyol-polyene compounds, CNQ140-996a, CNQ140-996b, CNQ140-996c and CNQ140-1010, each of which showed growth inhibition against the cancer cell line HCT-116 human colon carcinoma. The four antitumor-antibiotics had retention times of 26.3 min, 36.4 min, 43.5 min, and 51.6 min, respectively. Typical recoveries of the CNQ140 antitumor-antibiotics are 5-10 mg/L for each compound.

Compound Spectral and Physical Data for the Antitumor-Antibiotics from Marine Actinomycete Strain CNQ140.

CNQ140.996a: Yellow amorphous powder, $[a]_D+88°$ (c 0.05, EtOH); UV (EtOH) 325 sh ($\epsilon$=29000), 345 sh ($\epsilon$=41600), 359 ($\epsilon$=52000), 378 nm ($\epsilon$=44200); IR (neat) 3375, 2938, 2863, 1713, 1656, 1581, 1463, 1414, 1384, 1288, 1253, 1213, 1175, 1125, 1074, 1000, 969 cm$^{-1}$; HR MALDI-FT mass spectrum, obsd m/z 1019.5190 [M+Na]$^+$, $C_{58}H_{76}O_{14}$Na requires 1019.5133.

CNQ140.996b: Yellow amorphous powder, $[a]_D-286°$ (c 0.07, EtOH); UV (EtOH) 315 ($\epsilon$=55300) 340 ($\epsilon$=50300) nm; IR (neat) 3375, 2938, 1719, 1660, 1600, 1453, 1375, 1287, 1256, 1225, 1175, 1125, 1073, 1000, 978 cm$^{-1}$; HR MALDI-FT mass spectrum, obsd m/z 1019.5190 [M+Na]$^+$, $C_{58}H_{76}O_{14}$Na requires 1019.5133.

CNQ140.996c: Yellow amorphous powder, $[a]_D-161°$ (c 0.13, EtOH); UV (EtOH) 319 sh ($\epsilon$=40800), 345 sh ($\epsilon$=48300), 358 ($\epsilon$=53800), 375 ($\epsilon$=41400) nm; IR (neat) 3375, 2925, 1719, 1656, 1588, 1450, 1375, 1338, 1288, 1256, 1225, 1125, 1069, 1000, 975 cm$^{-1}$; HR MALDI-FT mass spectrum, obsd m/z 1019.5190 [M+Na]$^+$, $C_{58}H_{76}O_{14}Na$ requires 1019.5133.

CNQ140.1010: Yellow amorphous powder, [a]$_D$-233° (c 0.03, EtOH); UV (EtOH) 315 ($\epsilon$=58200), 340 ($\epsilon$=50600) nm; IR (neat) 3375, 2925, 1781, 1737, 1650, 1600, 1463, 1429, 1376, 1199, 1119, 1063, 1025, 978 cm$^{-1}$; HR MALDI-FT mass spectrum, obsd m/z 1033.4 [M+Na]$^+$, $C_{59}H_{78}O_{14}Na$ requires 1033.5289.

TABLE 2

$^1$H, $^{13}$C and HMBC NMR data of CNQ140.996a in pyridine-d$_5$

| Position | .δH mult (J$^g$, Hz)$^a$ | .δC$^b$ | HMBC$^a$ |
|---|---|---|---|
| 1, 1' | | 169.7 | |
| 2, 2' | | 122.7 | |
| 3, 3' | | 156.7 | |
| 4, 4' | 7.04 dd (8.2, 1.6) | 115.6 | 1 (1'), 3 (3'), 2 (2'), 6 (6'), 5 (5') |
| 5, 5' | 7.27 t (8.2) | 131.0 | 3 (3'), 7 (7'), 6 (6') |
| 6, 6' | 7.31 dd (8.2, 1.6) | 116.2 | 7 (7'), 2 (2'), 4 (4'), 8 (8'), 5 (5') |
| 7, 7' | | 137.0 | |
| 8, 8' | 7.24 d (15.5) | 129.5 | 7 (7'), 9 (9'), 10 (10'), 6 (6') |
| 9, 9' | 7.11 dd (15.5, 10.2) | 132.4 | 7 (7'), 11 (11'), 10 (10'), 8 (8') |
| 10, 10' | 6.49 dd (14.0, 10.2)$^f$ | 132.8 | 11 (11'), 12 (12'), 8 (8') |
| 11, 11' | 6.63 dd (14.0, 10.5)$^f$ | 135.7 | 12 (12'), 13 (13'), |
| 12, 12' | 6.52 dd (14.6, 10.5)$^f$ | 132.1 | 11 (11'), 10 (10'), 13 (13'), 14 (14') |
| 13, 13' | 6.74 dd (14.6, 11.0) | 131.2 | 15 (15'), 11 (11'), 12 (12'), 14 (14') |
| 14, 14' | 6.35 d br.d (11.0, 2.5) | 128.7 | 12 (12'), 13 (13'), 16 (16'), 29 (29') |
| 15, 15' | | 138.3 | |
| 16, 16' | 2.43 m$^{c,f}$ | 49.9 | 17 (17'), 18 (18'), 29 (29'), 15 (15'), 14 (14') |
| | 2.32 br d (12.2)$^f$ | | |
| 17, 17' | 4.29 br m$^{d,f}$ | 70.2 | |
| 18, 18' | 2.03 m$^e$ | 45.6 | 19 (19'), 17 (17'), 20 (20') |
| | 1.76 br d (14.2) | | |
| 19, 19' | 4.78 br m | 73.1 | |
| 20, 20' | 5.94 dd (15.0, 6.5) | 136.8 | 21 (21'), 19 (19'), 22 (22') |
| 21, 21' | 6.22 dd (15.0, 7.6) | 128.3 | 20 (20'), 19 (19'), 22 (22'), 23 (23') |
| 22, 22' | 2.50 m$^{c,f}$ | 42.6 | 23 (23'), 20 (20'), 21 (21') |
| | 2.38 m$^{c,f}$ | | |
| 23, 23' | 4.30 br m$^{d,f}$ | 67.8 | |
| 24, 24' | 2.10 m$^{e,f}$ | 44.5 | 23 (23'), 25 (25'), 26 (26'), 22 (22') |
| 25, 25' | 6.55 m | 71.7 | 1 (1') |
| 26, 26' | 2.18 br ddd (14.2, 6.5, 3.0) | 46.1 | 25 (25'), 24 (24'), 27 (27'), 28 (28') |
| | 2.00 m$^e$ | | |
| 27, 27' | 4.64 br m | 64.0 | |
| 28, 28' | 1.37 d (6.3) | 24.9 | 27 (27'), 26 (26'), |
| 29, 29' | 1.88 s | 17.8 | 16 (16'), 15 (15'), 13 (13'), 14 (14') |

$^a$300 MHz, pyridine-d$_5$.
$^b$75 MHz, pyridine-d$_5$.
$^{c-e}$Overlapping signals.
$^f$Chemical shifts were assigned using $^1$H-$^1$H COSY and homo-J-resolved $^1$H-NMR spectra.
$^g$Coupling constant determined by homo-J-resolved $^1$H-NMR spectroscopy.

TABLE 3

$^1$H and $^{13}$C NMR data of CNQ140.996b in pyridine-d$_5$ or CDCl$_3$

| position | .δH mult (J, Hz$^n$) 300 MHz, pyridine-d$_5$ | .δH mult (J, Hz$^n$) 400 MHz, CDCl$_3$ | HMQC (pyridine-d$_5$) | .δC (CDCl$_3$) |
|---|---|---|---|---|
| 1, 1' | | | 170.5 | 171.6 |
| 2, 2' | | | 122.2 | 110.8 |
| 3, 3' | | | 160.0 | 163.4 |
| 4, 4' | 7.06 dd (8.2) | 6.91 d (8.2) | 116.1 | 117.2 |
| 5, 5' | 7.32 t (8.2) | 7.34 t (8.2) | 132.0 | 134.5 |
| 6, 6' | 6.94 d (8.2) | 6.70 d (8.2) | 121.6 | 123.1 |
| 7, 7' | | | 139.2 | 140.8 |
| 8, 8' | 6.90 d (11.0) | 6.66 d (11.0) | 129.7 | 132.8 |
| 9, 9' | 6.43 m | 6.13 m$^f$ | 130.2 | 129.8 |
| 10, 10' | 6.60 m$^a$ | 6.23 m$^g$ | 128.0 | 128.2$^l$ |
| 11, 11' | 6.60 m$^a$ | 6.23 m$^g$ | 136.5 | 135.1 |
| 12, 12' | 6.19 dd like (14.6, 10.3)$^{b,m}$ | 6.13 m$^f$ | 128.3$^j$ | 128.4$^l$ |
| 13, 13' | 6.71 dd (14.6, 11.0) | 6.35 dd (14.6, 11.0) | 130.8 | 131.8 |
| 14, 14' | 6.22 br d (11.0, 2.5)$^{b,m}$ | 5.86 br d (11.0, 2.5) | 128.3$^j$ | 128.5$^l$ |
| 15, 15' | | | 139.0 | 135.7 |
| 16, 16' | 2.42 m$^{c,m}$ | 1.81 m$^{h,m}$ | 49.1 | 49.1 |
| 17, 17' | 4.35 br m$^{d,m}$ | 3.57 br tt (10.0, 4.0) | 68.8 | 70.4 |
| 18, 18' | 2.0-2.2 m$^e$ | 1.34 br d (15.5) | 44.6$^k$ | 44.2 |
| | 1.83 br dt (15.5, 3.5) | 1.08 m | | |
| 19, 19' | 4.71 br m | 3.91 br d (9.5) | 71.6 | 71.9 |
| 20, 20' | 5.91 dd (15.2, 5.9) | 5.29 br s$^i$ | 136.5 | 135.1 |
| 21, 21' | 6.13 dt (15.2, 7.5)$^b$ | 5.29 br s$^i$ | 127.4 | 128.6$^l$ |
| 22, 22' | 2.50 m$^{c,m}$ | 1.90 m | 42.0 | 41.1 |
| | 2.53 m$^{c,m}$ | | | |
| 23, 23' | 4.17 br m | 3.41 br tt (9.0, 4.5) | 67.0 | 66.7 |
| 24, 24' | 2.0-2.2 m$^e$ | 1.71 m$^{h,m}$ | 44.6$^k$ | 43.0 |
| 25, 25' | 6.30 m | 5.42 m | 72.2 | 73.5 |
| 26, 26' | 2.0-2.2 m$^e$ | 1.66 m$^{h,m}$/1.79 m$^{h,m}$ | 44.6$^k$ | 46.1 |
| 27, 27' | 4.38 br m$^{d,m}$ | 3.99 m | 64.0 | 65.0 |
| 28, 28' | 1.37 d (6.4) | 1.17 d (6.4) | 24.2 | 23.5 |
| 29, 29' | 1.92 s | 1.68 s | 17.8 | 17.3 |

TABLE 3-continued $^1$H and $^{13}$C NMR data of CNQ140.996b in pyridine-$d_5$ or CDCl$_3$

| position | δH mult (J, Hz$^n$) 300 MHz, pyridine-$d_5$ | δH mult (J, Hz$^n$) 400 MHz, CDCl$_3$ | HMQC (pyridine-$d_5$) | δC (CDCl$_3$) |
|---|---|---|---|---|
| OH | | 4.20 (4H, br s) | | |
|  | | 4.40 (2H, br s) | | |
| 3-OH | | 11.68 s | | |

$^{a-k}$Overlapping signal.
$^l$Interchangeable signals.
$^m$Chemical shifts were assigned by interpretation of $^1$H-$^1$H COSY spectral data.
$^n$Coupling constant determined by homo-J-resolved $^1$H-NMR spectroscopy.

TABLE 4

$^1$H and $^{13}$C NMR data of CNQ140-996c in CDCl$_3$

| position | δH mult (J, Hz)$^a$ | δC$^b$ | Position | δH mult (J, Hz)$^a$ | δC$^b$ |
|---|---|---|---|---|---|
| 1 | | 170.7 | 1' | | 171.7 |
| 2 | | 116.3 | 2' | | 110.4 |
| 3 | | 158.7 | 3' | | 163.2 |
| 4 | 6.81 d (8.2) | 116.3 | 4' | 6.92 d (8.1) | 117.1 |
| 5 | 7.24 t (8.2) | 132.8 | 5' | 7.36 t (8.1) | 134.3 |
| 6 | 7.01 d (8.2) | 118.0 | 6' | 6.71 d (8.1) | 123.0 |
| 7 | | 138.7 | 7' | | 140.3, |
| 8 | 6.89 d (14.7) | 130.8 | 8' | 6.69 d (10.6) | 132.4$^l$ |
| 9 | 6.66 dd (14.7, 10.0) | 132.5$^l$ | 9' | 6.16 m$^l$ | 129.8 |
| 10 | 6.30-6.50 m$^c$ | 129.6 | 10' | 6.30-6.50 m$^c$ | 128.2$^p$ |
| 11 | 6.30-6.50 m$^c$ | 134.6$^m$ | 11' | 6.30-6.50 m$^c$ | 134.7$^m$ |
| 12 | 6.31 m$^{c,q}$ | 131.4 | 12' | 6.16 m$^l$ | 128.4$^p$ |
| 13 | 6.40 m$^{c,q}$ | 131.8$^n$ | 13' | 6.40 m$^{c,q}$ | 131.6$^n$ |
| 14 | 5.97 d (10.4) | 127.9 | 14' | 5.88 d (11.0) | 128.5$^p$ |
| 15 | | 136.3$^o$ | 15' | | 136.1$^o$ |
| 16 | 2.00-2.10 m$^d$ | 49.6 | 16' | 1.80-2.10 m$^d$ | 48.3 |
| 17 | 3.80 m$^{e,q}$ | 69.4 | 17' | 3.55 br m$^{n,q}$ | 69.3 |
| 18 | 1.50-1.70 m$^f$ | 43.7 | 18' | 1.40 br d (15.0) 0.90 m$^q$ | 44.4 |
| 19 | 4.25 br m$^g$ | 73.5 | 19' | 4.02 br m$^{j,q}$ | 72.2 |
| 20 | 5.51 br s$^h$ | 135.6 | 20' | 5.35 br s$^k$ | 135.1 |
| 21 | 5.51 br s$^h$ | 127.9 | 21' | 5.35 br s$^k$ | 128.6$^p$ |
| 22 | 2.15 m$^{d,q}$ | 41.4 | 22' | 1.95 m$^{d,q}$ | 41.0 |
| 23 | 3.75 br m$^{e,q}$ | 66.7 | 23' | 3.46 br m$^{n,q}$ | 66.7 |
| 24 | 1.65-1.85 m$^f$ | 42.5 | 24' | 1.60-1.75 m$^f$ | 42.8 |
| 25 | 5.65 br m | 71.2 | 25' | 5.55 br m | 72.2 |
| 26 | 1.65-1.85 m$^f$ | 44.5 | 26' | 1.60-1.75 m$^f$ | 45.7 |
| 27 | 3.85 br m$^{e,q}$ | 64.1 | 27' | 3.95 br m$^{j,q}$ | 64.3 |
| 28 | 1.18 d (6.5) | 23.2 | 28' | 1.16 d (6.5) | 23.2 |
| 29 | 1.72 s | 17.7 | 29' | 1.68 s | 16.4 |
| OH | 4.25 br s$^g$ | | 3-OH | 11.55 s/9.82 br s | |
|  | 4.61 br s, 4.49 br s | | | | |

$^a$300 MHz, CDCl$_3$.
$^b$75 MHz, CDCl$_3$.
$^{c-k}$Overlapping signal.
$^{l-p}$Signals may be interchanged.
$^q$Chemical shifts were assigned by interpretation of the $^1$H-$^1$H COSY spectrum.

TABLE 5

$^1$H and $^{13}$C NMR data of CNQ140.1010 in CDCl$_3$

| position | δH mult (J, Hz)$^a$ | δC$^b$ | position | δH mult (J, Hz) | δC |
|---|---|---|---|---|---|
| 1, 1' | | 171.7 | 18, 18' | 1.34 br d (14.6)/1.11 m | 44.2 |
| 2, 2' | | 110.8 | 19, 19' | 3.90 br d (9.0) | 71.8 |
| 3, 3' | | 163.5 | 20, 20' | 5.28 br s$^e$ | 135.1 |
| 4, 4' | 6.91 d (8.1) | 117.2 | 21, 21' | 5.28 br s$^e$ | 128.6$^f$ |
| 5, 5' | 7.35 t (8.1) | 134.5 | 22, 22' | 1.91 m | 41.1 |
| 6, 6' | 6.70 d (8.1) | 123.1 | 23, 23' | 3.40 br t (9.0) | 66.8 |
| 7, 7' | | 140.8 | 24, 24' | 1.72 m | 43.0/43.9 |
| 8, 8' | 6.66 d (11.0) | 132.8 | 25, 25' | 5.43 m | 73.4/73.7 |
| 9, 9' | 6.13 m$^c$ | 129.9 | 26, 26' | 1.62 m/1.72 m | 46.1 |
| 10, 10' | 6.26 m$^d$ | 128.2$^f$ | 27, 27' | 3.98 br m/3.65 br m | 64.9/70.0 |
| 11, 11' | 6.26 m$^d$ | 135.1 | 28 | 1.17 d (6.6) | 23.5 |
| 12, 12' | 6.13 m$^c$ | 128.3$^f$ | 28' | 1.46 m | 30.4 |
| 13, 13' | 6.36 dd (14.6, 11.0) | 131.8 | 29, 30' | 1.68 s | 17.3 |
| 14, 14' | 5.86 br d (11.0) | 128.4$^f$ | 29' | 0.93 t (7.3) | 10.5 |
| 15, 15' | | 135.7 | | | |
| 16, 16' | 1.82 m | 49.1 | OH | 4.20 (4H, br m)/4.40 (2H, br s) | |
| 17, 17' | 3.57 br m | 70.4 | 3-and 3'-OH | 11.68 s/11.70 s | |

$^a$300 MHz, CDCl$_3$.
$^b$75 MHz, CDCl$_3$.
$^{c-e}$Overlapping signal.
$^f$Signals may be interchanged.

EXAMPLE 3

Screening Data from NCI 60 Cell Line Assay

Compounds CNQ140.996a, CNQ140.996b, and CNQ140.996c were examined in the National Cancer Institute's 60 cancer cell line, in vitro, cytotoxicity assay. The following cytoxicity data were derived for the invention compounds:

| Compound | Average GI50 against all 60 cell lines |
| --- | --- |
| CNQ140.996a | 18.6 nM |
| CNQ140.996b | 12.6 nM |
| CNQ140.996c | 5.1 nM |

Tissue Type Selectivity

Compounds CNQ140.996a, CNQ140.996b and CNQ140.996c all showed significant tissue type selectivity, with the most sensitive cancer types being 6 of the 8 melanoma cancer types (LOX IMVI, M14, SK-MEL-2, SK-MEL-5, UACC-257 and UACC-62). For all compounds, the most sensitive strain was SK-MEL-5 melanoma, which was approximately 500 times more sensitive than the average ($LC_{50}$=5.1 nM) for all 60 cell lines. Significantly, the compounds were only weakly active against all six leukemia strains in the 60 cell line panel.

Although the invention has been described with reference to the certain embodiments, it should be understood that various modifications can be made without departing from the spirit of the invention.

What is claimed is:

1. An isolated therapeutic marine actinomycete-derived isolated compound characterized as having
    a cyclic polyene-polyol structure comprising at least two aromatic moieties which are phenol derivatives, at least ten unsaturated moieties, and at least ten alcohol groups;
    a molecular weight from about 996 to about 1010 in the core ring structure;
    at least 58 carbons and at least 14 oxygens;
    and antitumor and/or anti-microbial activity, wherein the marine actinomycete is CNQ 140.

2. The compound of claim 1, wherein the compound has a chemical structure selected from:

-continued

3. An article of manufacture comprising:
packaging material; and
a pharmaceutical composition contained within the packaging material, wherein the packaging material includes a label indicating that the pharmaceutical composition includes at least one compound of claim 1.

4. The article of manufacture of claim 3, wherein the compound is selected from compounds having a chemical structure 5. An isolated therapeutic marine actinomycete-derived isolated compound having a chemical structure selected from a group consisting of:

and

-continued

6. The compound of claim 5, wherein the compound is isolated from a cultured marine actinomycete.

7. The compound of claim 5, wherein the marine actinomycetes is CNQ 140.

8. The compound of claim 5, wherein the compound is produced bio-synthetically.

9. The compound of claim 5, wherein the compound has anti-bacterial activity against drug-resistant pathogenic bacteria.

10. The compound of claim 5, wherein the compound has the degree of antibacterial activity that is at least equal to the degree of antibacterial activity of a macrolide, wherein the macrolide is selected from a group of macrolides that are capable of inhibiting nucleic acid synthesis in pathogenic bacteria.

11. The compound of claim 5, wherein the compound has antitumor activity against at least one melanoma cancer.

12. An article of manufacture comprising:
packaging material; and
a pharmaceutical composition contained within the packaging material, wherein the packaging material includes a label indicating that the pharmaceutical composition includes at least one compound of claim 5.

13. The compound of claim 10, wherein the nucleic acid synthesis in pathogenic bacteria is at the 50S ribosome.

* * * * *

UNITED STATES PATENT AND TRADEMARK OFFICE
CERTIFICATE OF CORRECTION

PATENT NO. : 7,521,414 B2 Page 1 of 1
APPLICATION NO. : 10/873657
DATED : April 21, 2009
INVENTOR(S) : Fenical et al.

It is certified that error appears in the above-identified patent and that said Letters Patent is hereby corrected as shown below:

Please delete the paragraph beginning on Line 11 of Column 1 and ending on Line 14 of Column 1 and replace with the following:

--This invention was made with government support under Grant No. CA44848 awarded by the National Institutes of Health, National Cancer Institute. The government has certain rights in the invention.--

Signed and Sealed this

Twenty-third Day of June, 2009

JOHN DOLL
*Acting Director of the United States Patent and Trademark Office*